United States Patent [19]

Adams et al.

[11] Patent Number: 5,211,817
[45] Date of Patent: May 18, 1993

[54] SEPARATION PROCESS

[75] Inventor: Stephen J. Adams, Warrington, Andrew M. Taylor, Chester, both of England

[73] Assignee: Imperial Chemical Industries PLC, London, England

[21] Appl. No.: 849,349

[22] Filed: Mar. 11, 1992

[30] Foreign Application Priority Data

Mar. 14, 1991 [GB] United Kingdom ................. 9105407

[51] Int. Cl.$^5$ ......................... B01D 3/00; C07C 17/00
[52] U.S. Cl. ....................................... 203/82; 203/99; 203/DIG. 19; 570/178
[58] Field of Search ............ 203/50, 82, 99, DIG. 19, 203/67; 570/178

[56] References Cited

U.S. PATENT DOCUMENTS

| 3,763,022 | 10/1973 | Chapman | 203/25 |
| 4,026,930 | 5/1977 | Bjornson | 570/178 |
| 4,166,774 | 9/1979 | Wagner | 203/82 |
| 4,256,541 | 3/1981 | Muller et al. | 203/25 |
| 4,299,606 | 11/1981 | Rabota et al. | 55/71 |
| 4,950,364 | 8/1990 | Wismer | 570/178 |

FOREIGN PATENT DOCUMENTS 0354697 2/1990 European Pat. Off. .

Primary Examiner—Virginia Monoharan
Attorney, Agent, or Firm—Cushman, Darby & Cushman

[57] ABSTRACT

A product stream containing, inter alia, HCl, HF and fluorocarbons which form close boiling point azeotropes with HF is subjected to distillation using sidestream rectification in order to effect energy efficient separation of selected fluorocarbon/HF azeotropes from one another.

8 Claims, 1 Drawing Sheet

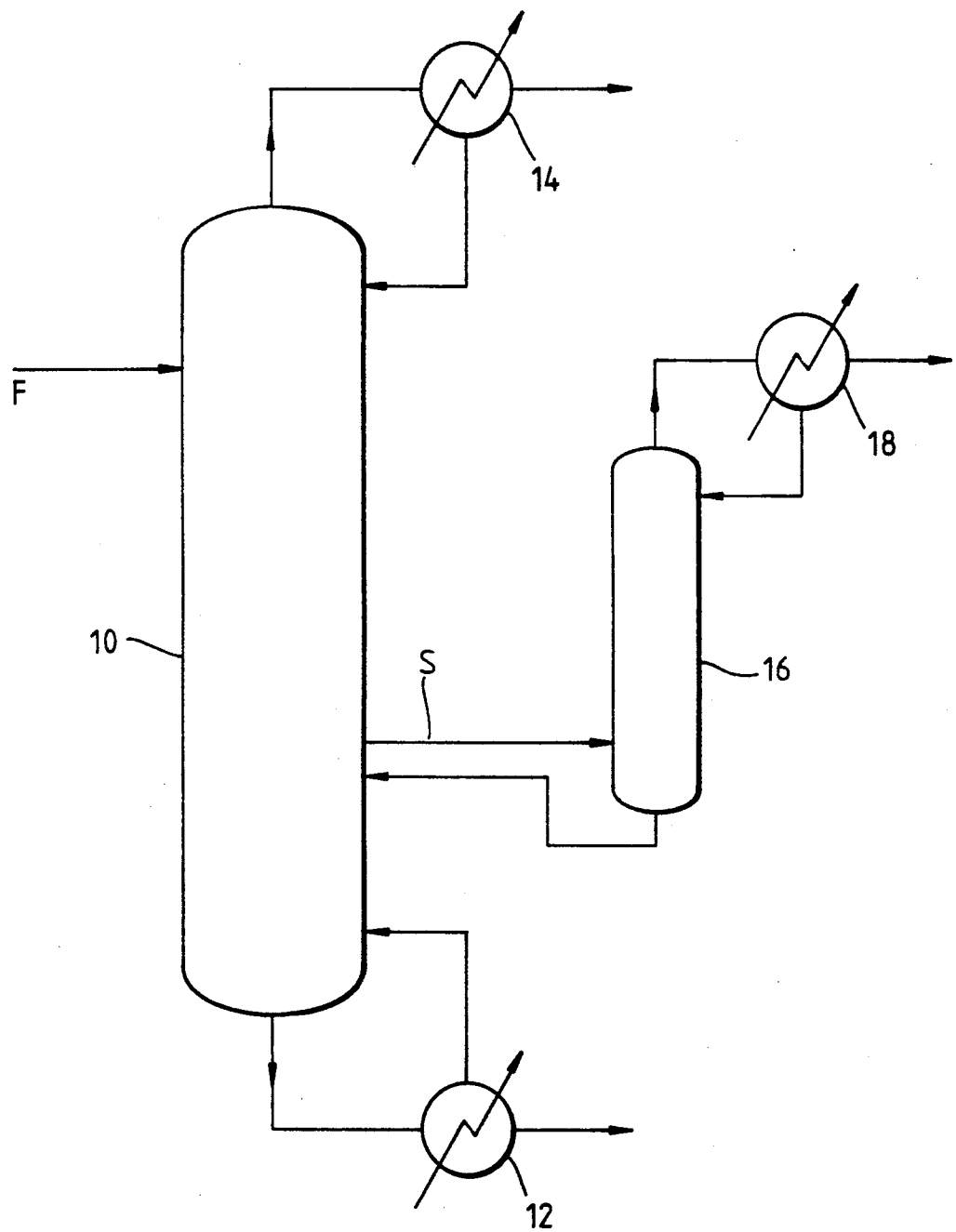

SEPARATION PROCESS

This invention relates to a separation process and particularly, but not necessarily exclusively, concerns the distillation of the product stream resulting from the fluorination of chlorofluorocarbons or chlorinated solvents where the product stream contains, inter alia, HCl, HF, and fluorocarbons such as 1,1,1,-trifluoroethane (143a). 1,1,1,2-tetrafluoroethane (134a). pentafluoroethane (125) and 2-chloro-1,1,1,2-tetrafluoroethane (124).

Although the separation of HCl and inerts, such as nitrogen, from the product stream can be effected by routine distillation in which the HCl and inerts constitute the lights while the other components form the bottoms, the separation of certain of the fluorocarbons, e.g. 143a from 134a or 125 from 134a, is complicated by the fact that, while such fluorocarbons have distinct boiling points, they form with HF azeotropic compositions with relative volatilities less than 1.5. Conventionally, such close boiling components would be separated by feeding the bottoms from the distillation column to a second distillation column to derive 125/HF or 143a/HF azeotropic composition as lights and the 134a/HF azeotropic composition as bottoms, the two azeotropic compositions thereafter each being subjected to azeotropic distillation in order to separate the fluorocarbons from HF.

The use of a second distillation column to effect the 125/HF:134a/HF or the 143a/HF:134a/HF split however is energy intensive since the relatively large feedstream to the second column has to be vaporised which means that the second column has to be equipped with a reboiler. In addition, the capital cost of the plant is substantial as a result of having to employ two distillation columns.

According to the present invention there is provided a process for the distillation of a product stream containing HCl, HF, and fluorocarbons which form close boiling azeotropes with HF and in which a lighter one of such fluorocarbons is present in an amount of no more than 20% by weight with respect to a heavier one of said fluorocarbons, said process comprising:

introducing the product stream into a main distillation column to separate said product stream into light ends containing HCl and heavy ends containing said fluorocarbons and HF;

withdrawing from the column a vapor sidestream containing the close boiling azeotropes of said fluorocarbons with HF; and introducing the sidestream into a rectifying column equipped with a condenser and operating with a high reflux ratio such that the lights derived from the rectifying column contain no more than 50% by weight of the heavier fluorocarbon azeotrope relative to the lighter fluorocarbon azeotrope, the heavy ends being re-introduced into the main distillation column.

According to a second aspect of the invention there is provided distillation plant for use in the distillation of a product stream containing HCl, HF, and fluorocarbons which form close boiling azeotropes with HF and in which a lighter one of such fluorocarbons is present in an amount of no more than 20% by weight with respect to a heavier one of said fluorocarbons, said plant comprising:

a main distillation column receiving said product stream as its feedstream and separating the product stream into light ends containing HCl and heavy ends containing said fluorocarbons;

a rectifying column equipped with a condenser;

means for withdrawing a vapour sidestream containing said fluorocarbon azeotropes from the main distillation column and introducing the same into the rectifying column; and means for re-introducing the heavy ends produced in said rectifying column into the main column;

the rectifying column being arranged to operate with a high reflux ratio such that the lights derived from the rectifying column contain no more than 50% by weight of the heavier fluorocarbon azeotrope relative to the lighter fluorocarbon azeotrope.

The heavier fluorocarbon may be constituted by 134a and the lighter fluorocarbon may be constituted by 143a or 125.

Preferably, in the product stream, the lighter fluorocarbon, e.g. 125 or 143a, is present in an amount of no more than 15%, more preferably no more than 10% and most preferably no more than 3%, by weight with respect to the heavier fluorocarbon, e.g. 134a.

Preferably the lights derived from the rectifying column contain no more than 40%, and more preferably no more than 30%, by weight of the heavier fluorocarbon relative to the lighter fluorocarbon.

The process of the invention is particularly advantageous where the product stream contains relatively small quantities of the lighter fluorocarbon (for example, the 143a or 125 content is typically of the order of a few thousand ppm, and each may be present in an amount of less than 3% by weight with respect to the 134a in the product stream) and this in turn allows sidestream rectification to be used with a high reflux ratio (typically of the order of 100:1). In this way, the need for a further distillation column with associated reboiler is avoided and substantial savings in energy consumption are possible.

Thus, in accordance with the invention, the main distillation column provides the rectifying and stripping sections for HCl versus 134a and the stripping section for 143a or 125 versus 134a and may be operated with a relatively low reflux ratio, while the rectifying column allows a large reflux ratio to be generated for the difficult separation, i.e. the rectifying of 143a/HF or 125/HF versus 134a/HF.

The invention will now be described by way of example only with reference to the accompanying drawing.

BRIEF DESCRIPTION OF THE DRAWING

The sole Figure is a diagrammatic representation of distillation plant in accordance with the invention.

DESCRIPTION OF THE PREFERRED EMBODIMENT

One embodiment of the invention is concerned with the distillation of a product stream resulting from the fluorination of a chlorofluorocarbon such that the product stream contains HCl, HF, 143a and/or 125, 124, 134a, nitrogen, and 133a.

The amount of 143a or 125 present is typically of the order of 3% by weight of the 134a present in the product stream.

The product stream is provided as the feedstream F to a main distillation column 10 having a reboiler 12 and a condenser 14, the column 10 being operated with a relatively low reflux ratio (typically in the range of 2.5:1 to 4:1)).

A number of the components in the feedstream F form azeotropic compositions with the HF present, namely 125, 143a, 134a, 124 and 133a. Of the components in the feedstream F, HCl forms the light key with the inerts such as nitrogen forming light ends while the azeotrope 125/HF forms the heavy key, the heavy ends being constituted by 143a/HF, 134a/HF, 124/HF, 133a/HF and HF. A vapor sidestream S is taken from the main column 10 at a location at or close to the point along the column height where the concentration of 143a is at its maximum value and the sidestream S is fed to a rectifying column 16 provided with a condenser 18. In the sidestream rectifier 16, the light key is constituted by 143a/HF with HCl and 125/HF as light ends while the heavy key is constituted by 134a/HF.

The rectifier 16 is operated with a relatively high reflux ratio such that the amount of 134a in the tops of the rectifier 16 is no greater than 50% by weight of the 143a present in the tops. Typically, the amount of 134a in the tops is of the order of 30% by weight of the 143a and the reflux ratio is of the order of 100:1.

The 143a/HF recovered from the rectifier 16 is fed downstream for subsequent processing, e.g. by way of azeotropic distillation. The bottoms from the rectifier 16 is recycled back to the main distillation column. The proportion of 143a in the reflux stream and hence recycled per unit time to the main column is somewhat greater than that recovered per unit time from the tops of the rectifier 16.

The bottoms from the main column is fed downstream for subsequent processing, involving for example azeotropic distillation.

The benefits of the above described distillation plant compared with a system involving two separate distillation columns include:

1. the need for only a single reboiler;

2. lower energy requirements since the large feedstream does not have to be vaporised twice and because the separation 143a/HF or 125/HF versus 134a/HF is made easier, hence requiring a lower condenser duty for this separation; and 3. the small size of the still needed for the difficult 143a/HF or 125/HF versus 134a/HF split.

I claim:

1. A process for the distillation of a product stream containing HCl, HF, and fluorocarbons which form close boiling azeotropes with HF and in which a lighter one of said fluorocarbons is present in an amount of no more than 20% by weight with respect to a heavier one of said fluorocarbons, said process comprising:

introducing the product stream into a main distillation column to separate said product stream into light ends containing HCl and heavy ends containing said fluorocarbons and HF;

withdrawing a vapor sidestream containing the close boiling azeotropes of said fluorocarbons with HF; and introducing the sidestream into a rectifying column equipped with a condenser and operating with a high reflux ratio such that the lights derived from the rectifying column contain no more than 50% by weight of the heavier fluorocarbon/HF fraction relative to the lighter fluorocarbon/HF fraction, the heavy ends being re-introduced into the main distillation column.

2. The process as claimed in claim 1 in which, in the product stream, the lighter one of said fluorocarbons is present in an amount of no more than 15% by weight with respect to the heavier one of said fluorocarbons.

3. The process as claimed in claim 1 in which, in the product stream, the lighter one of said fluorocarbons is present in an amount of no more than 10% by weight with respect to the heavier one of said fluorocarbons.

4. The process as claimed in claim 1 in which, in the product stream, the lighter one of said fluorocarbons is present in an amount of no more than 3% by weight with respect to the heavier one of said fluorocarbons.

5. The process as claimed in claim 1 in which the lights derived from the rectifying column contain no more than 40% by weight of the heavier fluorocarbon/HF fraction with respect to the lighter fluorocarbon/HF fraction.

6. The process as claimed in claim 1 in which the lights derived from the rectifying column contain no more than 30% by weight of the heavier fluorocarbon/HF fraction with respect to the lighter fluorocarbon/HF fraction.

7. The process as claimed in claim 1 in which the main distillation column is operated with a reflux ratio in the range of 2.5:1 to 4:1.

8. The process as claimed in claim 1 in which the heavier one of said fluorocarbons comprises 1,1,1,2-tetrafluoroethane and the lighter one of said fluorocarbons comprises 1,1,1-trifluoroethane.

* * * * *